US00PP28178P2

(12) United States Plant Patent
Hansen

(10) Patent No.: US PP28,178 P2
(45) Date of Patent: Jul. 11, 2017

(54) ***BUDDLEIA* PLANT NAMED 'BLUE KNIGHT'**

(50) Latin Name: ***Buddleia* hybrid**
Varietal Denomination: Blue Knight

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 14/999,594

(22) Filed: May 31, 2016

(51) Int. Cl.
*A01H 5/00* (2006.01)

(52) U.S. Cl.
USPC ..... Plt./242

(58) Field of Classification Search
USPC ..... Plt./242
See application file for complete search history.

*Primary Examiner* — Annette Para

(57) ABSTRACT

*Buddleia* 'Blue Knight' is a multiple-stemmed, densely-branched, short, compact, round-mounded habit, winter-hardy butterfly bush with many-flowered, long, thin thyrse over a long season beginning late-summer and continuing until about frost from soil line to top of plant. The sweetly fragrant dark purple flowers that are attractively offset by dark green foliage with silvery tomentose undersides.

1 Drawing Sheet

Botanical classification: *Buddleia* hybrid.
Variety denomination: 'Blue Knight'.

BACKGROUND OF THE PLANT

The present invention relates to the new and distinct butterfly bush plant, *Buddleia* 'Blue Knight' hybridized by Hans A. Hansen in the summer of 2010 at a wholesale perennial nursery in Zeeland, Mich., USA. 'Blue Knight' is the result of an ongoing breeding program conducted by the inventor. The goals for this program have been to produce improved, garden-worthy plants for the ornamental plant market. Seeds of the cross between *Buddleia* 'Podaras #8' U.S. Plant Pat. No. 22,069 as the female or seed patent and the male or pollen parent was presumably from *Buddleia* 'Blue Chip' U.S. Plant Pat. No. 19,991 and were harvested on Jun. 21, 2010. The new plant was selected as a single seedling and originally assigned breeder code H10-22-01.

No plants of *Buddleia* 'Blue Knight' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

*Buddleia* 'Blue Knight' was first asexually propagated from a single select plant in 2012 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

The following traits have been repeatedly observed and are determined to be the unique characteristics of 'Blue Knight'.

The nearest comparison plants are *Buddleia* 'Blue Chip' U.S. Plant Pat. No. 19,991, *Buddleia* 'Blue Chip Jr' U.S. Plant Pat. No. 26,581, 'Black Knight' (not patented) and the female parent. 'Blue Chip' is taller and wider in habit than 'Blue Knight'. The new plant has much greater vigor than 'Blue Chip Jr', is larger in height and width and has normal anthers and abundant pollen. Compared to 'Black Knight', the flower of the new plant is lighter and the habit of the new plant is more compact and much smaller in width and height.

Compared to the female parent, 'Podaras #8', the new plant produces pollen, the inflorescence is much larger but individual flower is smaller.

*Buddleia* 'Blue Knight' is a unique winter-hardy butterfly bush different from all other *Buddleia* cultivars known to the inventor based on the following combined traits:

1. Winter-hardy shrub, with multiple-stemmed, densely-branched, short, compact, round-mounded habit.
2. Many-flowered, long, thin thyrse over a prolonged season beginning late-summer and continuing to about frost from soil line to top of plant.
3. Sweetly fragrant, dark purple flowers.
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
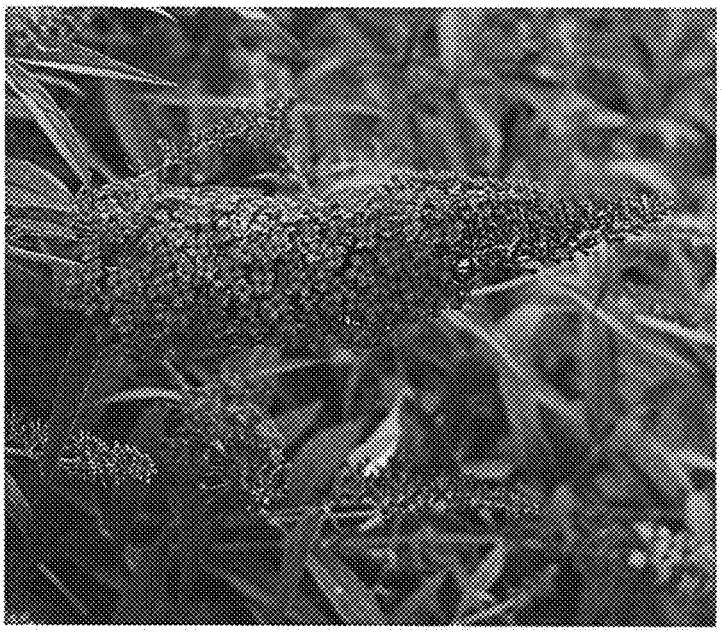
FIG. 1 shows a close-up of the flowers.
Figure 2:
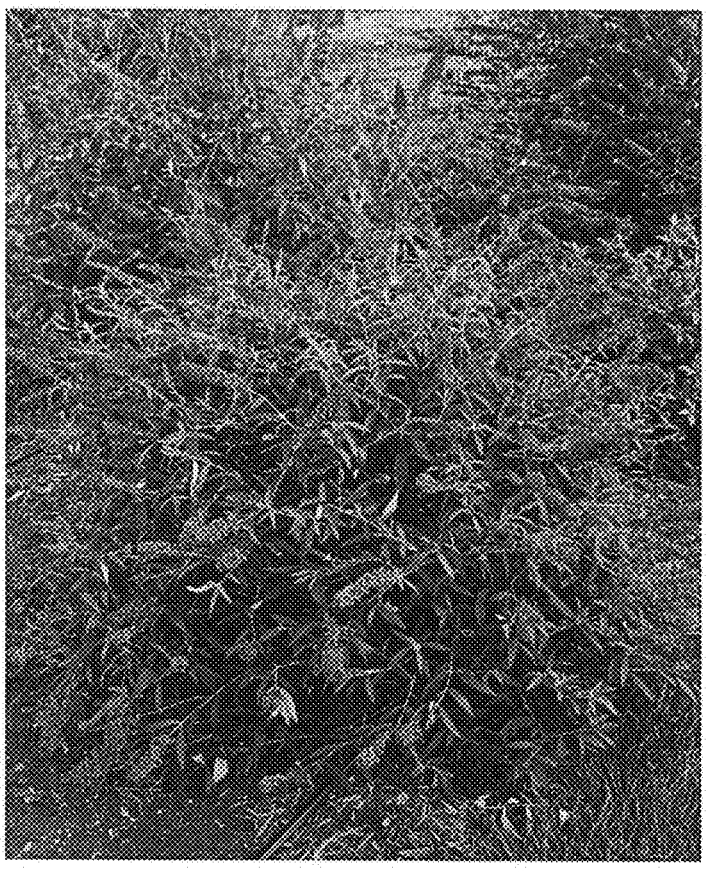
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Blue Knight', has not been observed under all possible environments. The phenotype may vary slightly with different environmental conditions, such as temperature, light, fertility, moisture and maturity levels, but without any change in the genotype. The following observations and size descriptions are of two-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering. The following traits have been repeatedly observed and are determined to be the unique characteristics of 'Blue Knight'.

Parentage: *Buddleia* 'Podaras #8' as the female or pod parent times presumably *Buddleia* 'Blue Chip' as the male or pollen parent.

Propagation:

*Method*.—Softwood cuttings.

*Time to initiate roots from tissue culture*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type.

*Crop time*.—Under normal spring growing conditions 6 to 7 weeks to fill and flower in a four-liter container a 65 mm liner; 8-10 weeks to finish and flower in a four-liter container from a 25 mm liner; Plant vigor is very good.

Plant description:

*Plant shape and habit*.—Winter-hardy, herbaceous, semi-woody, well-branched shrub with about 9 thick upright and branched main stems producing a compact rounded mound about 75 cm tall and about 100 cm wide at soil line.

*Stem*.—Tercte and woody in lower portion with slightly exfoliating bark; younger upper portion puberulent and quadrangular in cross section with ridges in corners; strong and flexible; average about 65 cm tall from soil line to just below terminal flowers, and about 8.0 mm diameter at the base; before distal flowers about 6 to 12 branches per main stem extending at about 80° angle from main stem.

*Stem color*.—Distal portion just below flowers between RHS 138C and RHS 138B with blushing of nearest RHS N77D in areas exposed to more intense light; basal woody portion blend between RHS 161A and RHS 165B with striations nearest RHS 200C.

*Plant size*.—Unpinched plant with stems flowering to about 75.0 cm tall; overall plant about 100.0 cm wide.

*Internode*.—About 14 nodes per stem below flowers, average internode length about 4.6 cm on unpinched plant; upper internodes slightly more elongated than lower internodes.

Foliage description: Opposite, decussate; serrulate; puberulent abaxial and adaxial; lanceolate with sharply attenuate base and sharply acute apex; no foliar fragrance detected.

*Leaf blade size*.—Up to about 9.5 cm long and about 1.8 cm wide, average about 6.5 cm long and about 1.2 cm wide; becoming smaller in distal portion of stem.

*Foliage color*.—Young expanding leaf adaxial side lighter than RHS 139A toward apex and between RHS 138A and RHS 138B toward base, young expanding abaxial nearest RHS 194A; mature leaves adaxial side blend between RHS 139A and RHS 147A and abaxial between RHS 148C and RHS 148B.

*Veins*.—Reticulate; abaxial raised, adaxial slightly impressed; puberulent to tomentose abaxial and glabrous adaxial.

*Vein color*.—Young expanding adaxial midrib nearest RHS 193A and lateral veins lighter than RHS 139A, abaxial young expanding midrib nearest RHS 145A; mature adaxial midrib nearest RHS 145C lateral veins nearest RHS 145C; abaxial midrib between RHS N144A and RHS 151A and lateral veins between RHS 139A and RHS 139B.

*Petioles*.—Glaucous and puberulent adaxial, pubescent abaxial; partially applanate top to bottom; average size about 2.0 mm long and about 1.0 mm wide at base; Petiole color: adaxial side blend between RHS 139A and RHS 147A and abaxial between RHS 152C and RHS 152D.

*Inflorescence description*.—Glomerate thyrse consisting of about 750 self-cleaning salverform flowers; to about 20.0 cm long and about 4.5 cm across; beginning in early August and continuing until late October in Michigan; attitude outward to slightly drooping.

*Buds*.—Elongated clavate, apex rounded; one day prior to opening about 8.0 mm total length and about 2.0 mm diameter in club, throat about 1.0 mm diameter in throat and about 6.0 mm long.

*Bud color*.—Nearest RHS 83A in club portion and tube portion blend between RHS N77A and RHS N77B.

*Sepals*.—Typically four, proximal two-thirds connate, adpressed to corolla tube; acute apex; glabrous adaxial and puberulent abaxial; margin entire, edentate; fused in about the basal 1.6 mm and split in about the terminal 0.9 mm; forming a corolla about 2.5 mm long and about 1.0 mm across; individually less than about 1.0 mm wide at point of fusion.

*Sepal color*.—Adaxial nearest RHS 138C, abaxial between RHS 145A and RHS 139C heavily tinted with nearest RHS N187A.

*Flower fragrance*.—Pleasantly and distinctly sweet.

*Flower attitude*.—Upward and outward.

*Lastingness of inflorescence*.—About 8 to 10 days.

*Lastingness of individual flower*.—About 3 to 5 days.

*Petals*.—Typically four; glabrous; fused into salverform with typically straight cylindrical tube about 8.0 mm long and 1.0 mm diameter, and a flattened face about 6.0 mm across; petal blade rounded with crenate margin; blade to about 2.5 mm across and about 2.0 mm long from fused face; center flattened face portion of corolla about 2.0 mm.

*Petal color*.—Basal 1.0 mm of abaxial tube lighter than RHS 155D, center portion of abaxial tube between RHS N77B and RHS N77C, abaxial petal blades nearest RHS 83B with thin rim of nearest RHS 86A; adaxial tube basal 1.0 mm nearest RHS 151B with center tube blend of between RHS 174D and RHS 84B, adaxial face blades nearest RHS 83B with a thin rim of nearest RHS 86A.

*Gynoecium*.—Pistil: one; about 3.0 mm long. Style: short, round, glabrous; about 1.5 mm long and less than 0.2 mm diameter; color nearest RHS 145C. Stigma: oblong, minutely puberulent; about 0.5 mm in diameter and about 1.0 mm long; color nearest RHS 144B. Ovary: superior; oblong; about 0.5 mm across at base and 1.0 mm tall; distally tapering to style; color nearest RHS 145A.

*Androecium*.—Filaments: not produced or very short. Anthers: typically four; oblong; introrse; adnate to about mid-point of corolla tube; about 1.0 mm long and 0.5 mm wide; color nearest RHS 158B. Pollen: abundant, globose, less than 0.1 mm long; color nearest RHS 4D.

*Pedicel*.—Short, puberulent; about 2.0 mm long and about 0.5 mm diameter; color nearest RHS 158D.

*Peduncle*.—Quadrangular, pubescent to tomentose, flexible and strong; flowering portion to about 20.0 cm long.

*Peduncle color*.—Between RHS 138D and RHS 138C.

*Fruit*.—Fruit set has not been observed.

*Seed*.—Not yet observed.

Disease resistance: *Buddleia* have been noted to resist deer browsing. Other resistance beyond that of known butterfly bush cultivars has not been observed. The plant grows best with plenty of moisture and adequate drainage, but is able to tolerate some drought when mature. Hardiness at least from USDA zone 5 through 10.

The invention claimed is:

1. A new cultivar of winter-hardy butterfly bush *Buddleia* plant named 'Blue Knight' as herein illustrated and described, especially suitable for potted plant culture, landscaping as a specimen or en masse or as cut flower purposes.

* * * * *